United States Patent [19]

Härle

[11] Patent Number: 5,147,363

[45] Date of Patent: Sep. 15, 1992

[54] SCREW FOR USE IN OSTEOSYNTHESIS

[76] Inventor: Anton Härle, Drechslerweg 40, D-4400 Münster, Fed. Rep. of Germany

[21] Appl. No.: 629,996

[22] Filed: Dec. 19, 1990

[30] Foreign Application Priority Data

Dec. 21, 1989 [DE] Fed. Rep. of Germany ....... 3942326

[51] Int. Cl.$^5$ ............................................. A61B 17/53
[52] U.S. Cl. ........................................ 606/73; 606/72
[58] Field of Search ...................... 606/72, 73, 53, 59, 606/60, 61, 63, 69

[56] References Cited

U.S. PATENT DOCUMENTS

| 324,768 | 8/1885 | Hunt | 606/72 X |
|---|---|---|---|
| 3,236,141 | 2/1966 | Smith | 606/73 X |
| 3,466,748 | 9/1969 | Christensen | 606/73 X |
| 4,463,753 | 8/1984 | Gustilo | 606/73 |
| 4,468,200 | 8/1984 | Münch | 606/73 X |
| 4,493,317 | 1/1985 | Klaue | 606/73 X |
| 4,569,338 | 2/1986 | Edwards | 606/73 |
| 4,887,595 | 12/1989 | Heinig et al. | 606/73 X |

FOREIGN PATENT DOCUMENTS

| 181433 | 5/1986 | European Pat. Off. . | |
| 201024 | 11/1986 | European Pat. Off. . | |
| 325682 | 8/1989 | European Pat. Off. . | |
| 1266386 | 5/1961 | France | 606/73 |
| 2015346 | 9/1979 | United Kingdom . | |
| 9002526 | 3/1990 | World Int. Prop. O. | 606/73 |

Primary Examiner—Robert A. Hafer
Assistant Examiner—Sam Rimell
Attorney, Agent, or Firm—Peter K. Kontler

[57] ABSTRACT

An osteosynthetic screw for the setting of bones or bone fragments has an osteological thread zone and a handle. Stability at the so-called stress points of the screw is improved and the design of the screw is changed to obtain better contact. Finally, angularly stable attachment to the osteological plate is possible.

11 Claims, 3 Drawing Sheets

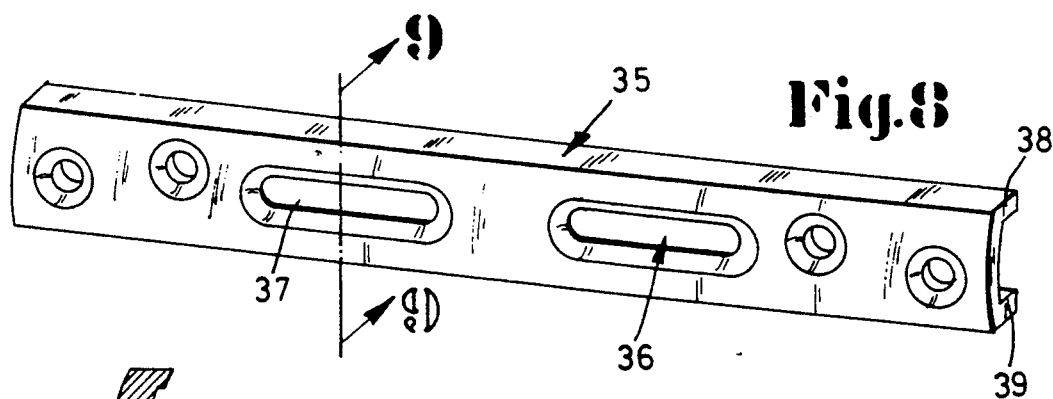
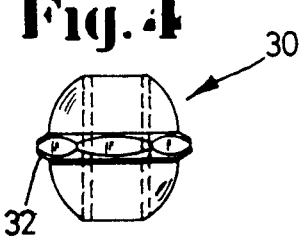
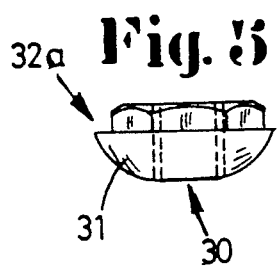
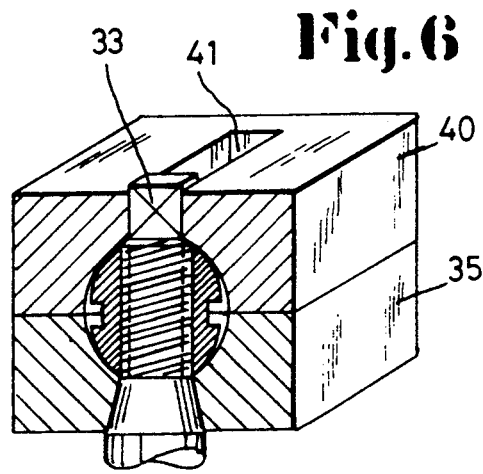
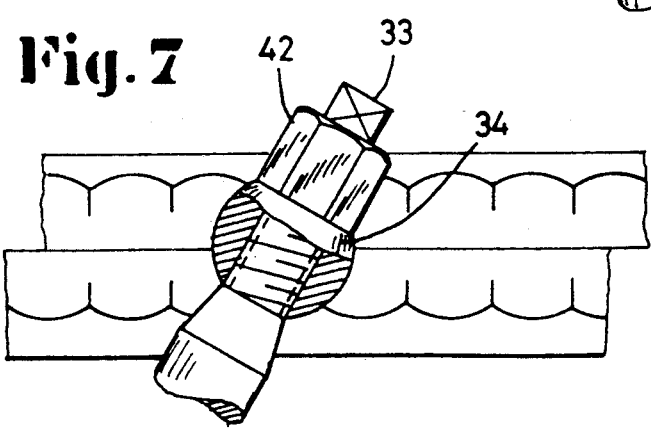

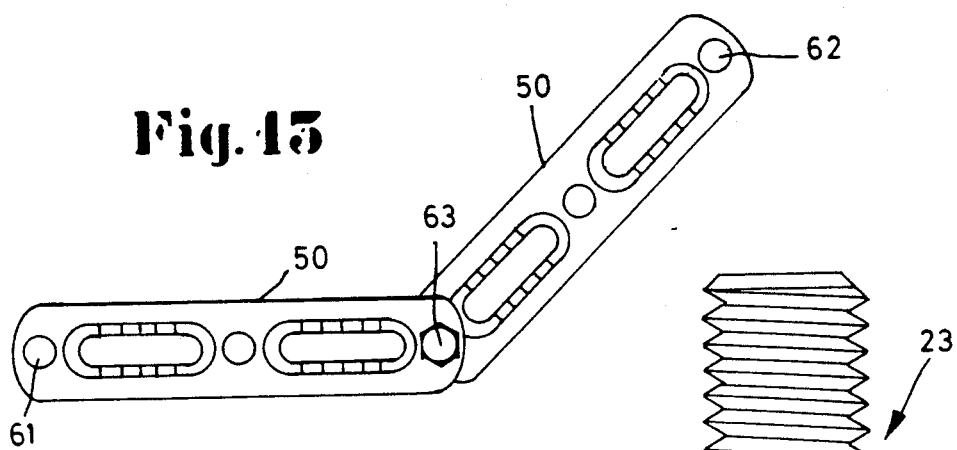
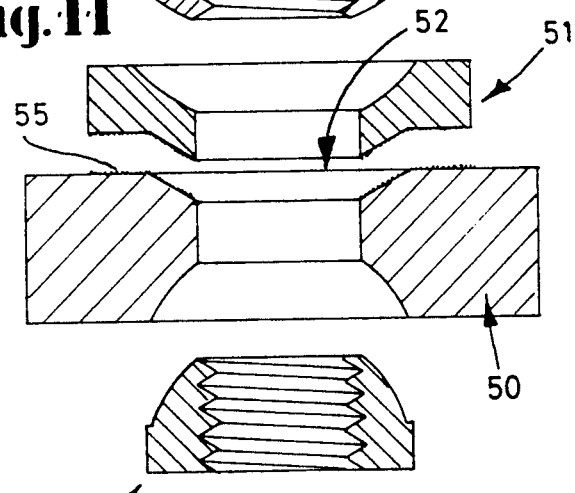
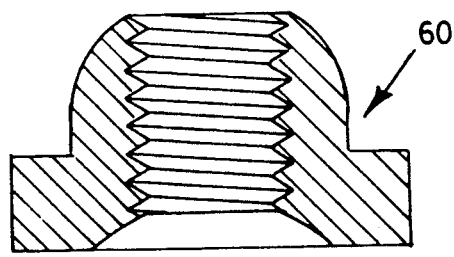
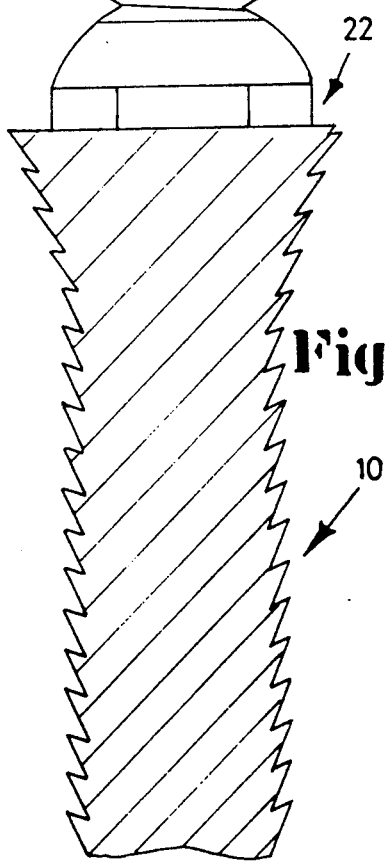

SCREW FOR USE IN OSTEOSYNTHESIS

BACKGROUND OF THE INVENTION

The invention relates to screws and to plates for use in osteosynthesis.

Osteological screws, as well as osteological pins having a threaded portion for bones, are mostly used in combination with plate and rod systems to fix bones and bone segments in specific position and alignment relative to on another.

During conventional osteosynthesis on tubular bones, a plate provided with holes is fixed to the bone by means of osteological screws which pass through these holes. Immobilization of the bone or bone segments is carried out by pressing the same against the plate via screws. The screw holes are countersunk on the side opposite the bone where they constitute an abutment for the heads of the screws. Stable connection of the bones or bone segments is thus achieved by pressing of the screw heads against the osteological plate and the resulting secondary pressing of the osteological plate against the bone itself. The osteological screws anchored in the bone are subjected to practically pure tension within the bone itself since the bending forces in this area are absorbed by the bone tissue. Much greater mechanical forces, especially bending loads, arise at the exit point of the screws from the bone. The transition of the osteological thread of conventional screws accordingly constitutes a stress concentration. The material is additionally weakened by a recess which is intended for a tool and projects into the neck of the screw.

In clinical practice, therefore, screw fractures are constantly seen and typically occur at these weakened locations. Inasmuch as the broken portion of the screw remaining in the bone is practically flush with the surface of the bone and does not present a gripping area, relatively large bores, which weaken the bone considerably, must be formed in the bone by means of hollow drills in order to remove the broken portion.

In setting procedures using threaded osteological pins which are fixed to rod systems via a lateral connection, such fractures occur somewhat less frequently because of the greater elasticity and the lower stress concentration existing with large contact areas. Nevertheless, the longer lever arm and the greater distance between the exit point from the bone and the fixing location at the rod system leads to bending of the pins and, consequently, to inadequate fixing of the bone or bone segments. The results are undesired changes in position and failure of the bone to heal.

In procedures involving the application of plates to the spinal column, stressing of the osteological screws at the transition to the screw head is still greater since the anatomical characteristics allow each bone to be fixed to the osteological plate by a single osteological screw only. Stability is further reduced because the osteological plates cannot be pressed against the bone contact surfaces over a large area to thereby compensate for part of the bending load by tension/compression stressing. Since, on the one hand, substantial forces and loads arise (virtually the entire body weight bears on a fixing screw) while, on the other hand, pressure between plate and bone and, secondarily, between plate and screw, is greatly reduced, the immobilization required for bone consolidation frequently cannot be achieved. Due to the point overloading of the screws in conjunction with the increased bending load, they loosen or fracture much more often than in osteosynthesis at the extremities. Loosening, in turn, is caused by the fact that solid anchoring occurs only in the region of contact of the osteological screw with cortical structures ( rind of the bone). Whereas the screws are always anchored in two bone rinds with the tubular bones of the extremities, the screws are screwed through the narrow, bony connections between the anterior vertebral bodies and the lateral vertebral arches during setting of the spine. These bony bridges, referred to as arch roots (pedicels), have the form of a yarn spool and it is exclusively in the middle, i.e., narrow, portion that good, direct force transmission to the centrally extending osteological screw, which only here tangentially contacts the rind of the bone, can be achieved. Substantial force transmission is hardly possible dorsally of this isthmus and in particular, there is no bone rind to support the osteological screw at its exit point.

Stable setting of the spinal column is difficult to begin with and possible only when the thread of the osteological screw directly contacts the pedicel-corticalis in the region of the isthmus. The stress concentration, which is naturally a function of how solidly the screw is anchored in the bone, occurs either at the heat of the screw or, more often, several millimeters from the head of the screw where the screw loses contact with the isthmus-corticalis. These concentrations are highly likely to cause screw fratures in the posterior pedicel region in about 10% of clinical applications, especially when there is angularly stable anchoring of the osteological screws to an osteological plate. The fractures occur approximately 2 to 8 mm before the exit point of the screw from the pedicel, i.e., in the latter. Due to the close proximity of the spinal cord, such complications are particularly problematical and difficult to control.

OBJECTS OF THE INVENTION

It is an object of the invention to provide an osteosynthetic screw which has greater stability and permits better connection of additional accessories to be achieved.

Another object of the invention is to provide a novel and improved osteosynthetic device which utilizes the improved screw.

Advantageous embodiments are set forth in the subclaims.

SUMMARY OF THE INVENTION

It is proposed that the screw or threaded pin have a reinforcement at the transition from the zone of the osteological thread to the manipulating portion.

It is further proposed to provide a reinforcement in the manipulating zone which serves as a spacer and, at the same time, creates an abutment surface for the bone and an abutment surface for a plate to be attached. This reinforcement zone can also have a holding fixture for a so-called positionator.

According to another feature of the invention, the reinforcement can be a sleeve which cooperates with the transition from the osteological thread zone to the manipulating portion and stabilizes this area. This sleeve can have an internal thread which cooperates with the osteological thread or the machine thread of the screw and is designed externally as has been or will be described with reference to the screw.

In addition, a connecting device for an osteological hook can be provided on the screw.

BRIEF DESCRIPTION OF THE DRAWING

FIG. 4 shows a first embodiment of a nut which cooperates with the machine thread zone of the screw, FIG. 5 shows another embodiment of a nut, FIG. 6 shows the placement of the nut on a screw together with an osteosynthetic plate and a cover plate, FIG. 7 shows the placement of a screw at an inclination to the direction of the longitudinal axis of two plates, FIG. 8 shows an osteosynthetic plate, FIG. 9 is a section along the line 9—9 of FIG. 8, FIG. 10 shows an embodiment of the screw according to the invention on an enlarged scale, FIG. 11 is an exploded view illustrating certain individual components, FIG. 12 shows a sleeve and FIG. 13 shows two osteosynthetic plates, on a reduced scale, which are connected to one another.

DESCRIPTION OF PREFERRED EMBODIMENTS

Figure 1:
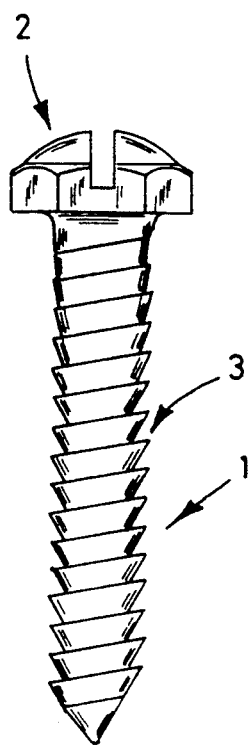
FIG. 1 shows a screw in which the osteological thread zone is generally cylindrical but its upper portion next the handle.

FIG. 1 shows a screw having an osteological thread zone 1 and a handle 2. The thread 3 of the osteological thread zone 1 is less deep in the upper region before the handle than in the lower region and thus increases the torsional resistance of the screw in the region before the handle. Depending upon the application, this strengthened region can constitute 1% to 50% of the osteological thread zone 1.

Figure 2:
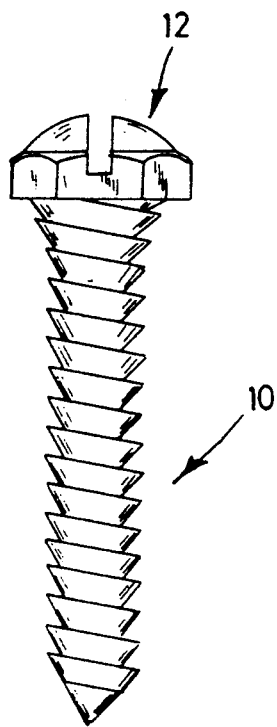
FIG. 2 shows a screw in which the osteological thread zone diverges conically towards the handle in the upper portion.

In the exemplary embodiment illustrated in FIG. 2, the osteological thread zone 10 widens towards the handle 12, i.e., the screw diverges conically in the region thereof before the handle. The required torsional resistance of the screw in this region is achieved in this manner.

Figure 3:
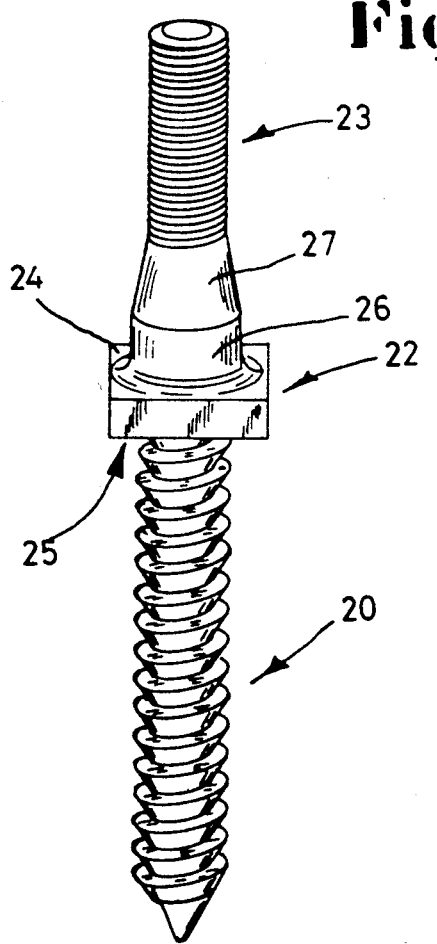
FIG. 3 shows a screw in which an extension adjoins the handle.

FIG. 3 shows a screw in which, for the sake of simplicity, a reinforcement of the osteological thread zone is not illustrated.

The screw shown in FIG. 3 has an osteological thread zone 20. A handle 22 which, in the illustrated exemplary embodiment, is constructed as a quadrangular plate adjoins the osteological thread zone 20. Such a quadrangular plate provides a flat upper surface zone 24 and a flat lower surface zone 25 and accordingly makes it possible to apply a manipulating tool which embraces the quadrangular plate in a fork-like fashion and is thus open on one side only and surrounds the handle on three sides.

A cylindrical zone 26 adjoins the handle 22 and functions as a reinforcement as well as a support for an osteosynthetic accessory such as, for example, a plate or a fixator. An extension including machine thread zone or sections 23 adjoins this cylindrical zone 26 and the transition from the cylindrical zone 26 to the machine thread zone 23 is constructed as a conically converging end zone 27. If this end zone 27 is, in particular, conical and convex, the osteosynthetic plate can also be connected at an angle to the longitudinal axis of the screw.

FIGS. 4 to 7 show a nut 30 which can be used together with the screw illustrated in FIG. 3. The nut 30 shown in FIG. 4 has two spherical zones and a manipulating zone 32 while the nut illustrated in FIG. 5 has only a single spherical zone 31 and a manipulating zone 32a which is set back from the spherical zone. Appropriate osteosynthetic devices such as, for instance, the osteosynthetic plate 35 shown in FIG. 8, can be supported on the spherical zones of these nuts.

Such support is illustrated in FIGS. 6 and 7. The actual osteosynthetic plate 35, which can also be referred to as an osteological plate, is seen in FIG. 6 as is a so-called cover plate 40 of the prior art (European patent application 201 024).

The cover plate 40 is provided with a slit 41 and the upper end 33 of the actual osteological screw projects into the slit 41. This upper end 33 is polygonal. The cover plate 40 thus simultaneously serves to prevent rotation.

FIG. 7 makes it clear that the design of the nuts 30, and especially of the zones of the osteosynthetic plate 35 which cooperate therewith, allows the osteological screw to be inserted at an inclination. In FIG. 7, a supporting sphere 34 is screwed onto the machine thread zone 23 of the osteological screw. This supporting sphere 34 can be fixed by a lock nut 42. Here, also, the upper end 33 of the screw is polygonal.

FIGS. 8 and 9 show an osteological plate or osteosynthetic plate 34 which, among other things, has elongated openings 36 and 37.

In contrast to the prior art, the plate is equipped with flanges 38 and 39 which, for example, bear against the upper side of the bone. Accordingly, full surface contact of the plate no longer occurs.

In order that the plate may be held even in the absence of contact with the bone, a conical flare is provided at the underside of the elongated openings 36 and 37 in the region of the elongated openings. The conical flare can have spherical "nestings" so that good support is obtained, e.g., at the upper side of the nut 30 of FIG. 4.

It is important to point out that the conical flare of the elongated openings 36 and 37 can be provided only at the underside, only at the upper side or at both the upper side and lower side of the elongated openings. When spherical "nestings" are provided in the region of the conical recesses, the upper and lower ones can be offset relative to one another on the longitudinal axis of the osteological plate 35.

FIG. 10 illustrates an osteological screw according to the invention whose osteological thread 10 becomes thicker from the normal zone towards the handle 22 while the depth of the thread remains the same. The increase in radius or diameter occurs along a curve, i.e., the residual, cylindrical, osteological thread zone diverges upwards towards the handle 12 in a tulip-like manner.

FIG. 11 shows an osteosynthetic plate 50 and, in conformance with the arrangement of FIG. 8, an elongated hole 52 of the osteological plate 50 is visible. The underside of the elongated hole is spherical whereas the upper side diverges outwards linearly and conically. A cooperating surface of a nut 53 which is likewise spherical thus fits into the spherical recess of the underside so that pivoting is possible. These pivotal movements are also followed by a nut 54 which again has a spherical configuration on the side thereof facing the plate 50. A washer 51 can be interposed between the nut 54 and the plate 50, and the underside of the nut 54 is congruent to the linearly and conically diverging surface of the osteosynthetic plate 50 while the upper side thereof is spherical in conformance with the nut 51.

The underside of the washer 51 and the corresponding, cooperating zone of the osteosynthetic plate 50 can be roughened as indicated at 55.

FIG. 12 shows a sleeve 60 having a lower, spherical recess and an upper, spherical arch.

FIG. 13 illustrates two osteosynthetic plates 50 which have bores 61 and 62 at their ends and can be connected to one another by screws of which one can be seen at 63. This makes it possible to form angles which can better conform to the shape of the bone or the spinal column.

I claim:

1. An osteosynthetic screw for setting bones or bone fragments, comprising an osteological thread zone, an extension for coupling the screw to an ostesynthetic accessory, and a threadless handle between said zone and said extension, said zone including a divergent reinforcing portion which is adjacent said handle and has a diameter which increases toward said handle, said portion of said zone extending radially outwardly beyond said handle.

2. The screw of claim 1, wherein said divergent portion of said zone has a first length and said zone includes a second portion having a second length which is at least 30 percent of the length of said zone, said divergent zone being disposed between said handle and said second portion.

3. The screw of claim 1, wherein said extension includes a polygonal outline, said second being disposed between said end portion and said handle.

4. The screw of claim 1, wherein said zone has an external thread of constant depth measured radially of said zone.

5. The screw of claim 1, wherein said handle includes an unthreaded portion which is adjacent said extension.

6. The screw of claim 1, wherein said handle includes a sleeve.

7. The screw of claim 6, wherein said extension includes an externally threaded section and said sleeve has internal threads and mates with said section.

8. The screw of claim 1, wherein said extension includes an externally threaded section and further comprising a nut mating with said section and having at least one spherical external surface.

9. The screw of claim 8, wherein said nut has a plurality of spherical external surfaces.

10. The screw of claim 8, wherein said nut includes a handle.

11. The screw of claim 1, wherein said extension includes an externally threaded section and further comprising an internally threaded supporting sphere mating with said section.

* * * * *